US005856515A

United States Patent [19]
Therien et al.

[11] Patent Number: 5,856,515
[45] Date of Patent: Jan. 5, 1999

[54] ELECTRON-DEFICIENT PORPHYRINS AND PROCESSES AND INTERMEDIATES FOR PREPARING SAME

[75] Inventors: Michael J. Therien, Philadelphia, Pa.; Stephen DiMagno, Lincoln, Nebr.

[73] Assignee: Trustees of the University of Pennsylvania, Philadelphia, Pa.

[21] Appl. No.: 763,766

[22] Filed: Dec. 11, 1996

Related U.S. Application Data

[60] Division of Ser. No. 234,651, Apr. 28, 1994, Pat. No. 5,599,924, which is a continuation-in-part of Ser. No. 64,468, May 20, 1993, Pat. No. 5,493,017, which is a continuation-in-part of Ser. No. 929,943, Aug. 14, 1992, Pat. No. 5,371,199.

[51] Int. Cl.$^6$ ........................ C07D 209/00; C07D 207/00
[52] U.S. Cl. ........................... 548/400; 548/517; 548/518
[58] Field of Search .................................. 548/400, 517, 548/518

[56] References Cited

U.S. PATENT DOCUMENTS

| | | | |
|---|---|---|---|
| 3,579,533 | 5/1971 | Yalman | 260/314 |
| 3,687,863 | 8/1972 | Wacher | 252/300 |
| 3,897,255 | 7/1975 | Erickson | 96/115 R |
| 3,899,334 | 8/1975 | Erickson | 96/48 R |
| 4,360,703 | 11/1982 | Bolton et al. | 136/263 |
| 4,647,478 | 3/1987 | Formanek et al. | 427/164 |
| 4,657,902 | 4/1987 | Kappas et al. | 514/185 |
| 4,668,670 | 5/1987 | Rideout et al. | 514/185 |
| 4,792,836 | 12/1988 | Quinlan | 357/30 |
| 4,892,941 | 1/1990 | Dolphin et al. | 540/145 |
| 4,895,682 | 1/1990 | Ellis, Jr. et al. | 260/410.9 R |
| 4,957,615 | 9/1990 | Ushizawa et al. | 204/415 |
| 4,970,348 | 11/1990 | Ellis, Jr. et al. | 568/399 |
| 4,986,256 | 1/1991 | Cohen et al. | 128/653 |
| 4,988,808 | 1/1991 | Morgan et al. | 540/145 |
| 5,051,337 | 9/1991 | Sakoda et al. | 430/270 |
| 5,091,502 | 2/1992 | Narang et al. | 528/229 |
| 5,103,027 | 4/1992 | Shum et al. | 549/329 |
| 5,118,886 | 6/1992 | Ellis, Jr. et al. | 568/910 |
| 5,120,453 | 6/1992 | Frame et al. | 210/759 |
| 5,120,882 | 6/1992 | Ellis, Jr. et al. | 568/910 |
| 5,120,886 | 6/1992 | Lyons et al. | 568/909.8 |
| 5,164,944 | 11/1992 | Benton et al. | 371/40.1 |
| 5,169,944 | 12/1992 | Nelson et al. | 540/145 |
| 5,171,741 | 12/1992 | Dougherty | 514/185 |
| 5,200,481 | 4/1993 | Sounik et al. | 526/259 |
| 5,212,300 | 5/1993 | Ellis, Jr. et al. | 540/145 |
| 5,241,062 | 8/1993 | Wijesekera et al. | 540/145 |
| 5,252,730 | 10/1993 | Mackey | 540/140 |
| 5,280,115 | 1/1994 | Ellis, Jr. et al. | 540/145 |
| 5,371,199 | 12/1994 | Therien et al. | 540/145 |
| 5,405,957 | 4/1995 | Tang et al. | 540/472 |

FOREIGN PATENT DOCUMENTS

| | | |
|---|---|---|
| 0 161 606 A2 | 11/1985 | European Pat. Off. . |
| 0 168 994 A2 | 1/1986 | European Pat. Off. . |
| 0 172 427 A2 | 2/1986 | European Pat. Off. . |
| 0 340 968 A2 | 11/1989 | European Pat. Off. . |
| 0 384 503 A1 | 8/1990 | European Pat. Off. . |
| 0 390 523 A2 | 10/1990 | European Pat. Off. . |
| 0 393 575 A1 | 10/1990 | European Pat. Off. . |
| 0 428 214 A1 | 5/1991 | European Pat. Off. . |
| 0 442 060 A2 | 8/1991 | European Pat. Off. . |
| 0 461 542 A2 | 12/1991 | European Pat. Off. . |
| 0 464 717 | 1/1992 | European Pat. Off. . |
| 0 471 561 A2 | 2/1992 | European Pat. Off. . |
| 0 477 402 A1 | 4/1992 | European Pat. Off. . |
| 0 480 361 A2 | 4/1992 | European Pat. Off. . |
| 0 494 508 A1 | 7/1992 | European Pat. Off. . |
| 3827640 | 8/1988 | Germany . |
| 6-128263 | 10/1994 | Japan . |
| 2225963 | 6/1990 | United Kingdom . |
| WO 85/01617 | 4/1985 | WIPO . |
| WO 87/00023 | 1/1987 | WIPO . |
| WO 89/10772 | 11/1989 | WIPO . |
| WO 89/11277 | 11/1989 | WIPO . |
| WO 91/04029 | 4/1991 | WIPO . |
| WO 91/07659 | 5/1991 | WIPO . |
| WO 91/09631 | 7/1991 | WIPO . |
| WO 91/16820 | 11/1991 | WIPO . |
| WO 91/18006 | 11/1991 | WIPO . |
| WO 91/18007 | 11/1991 | WIPO . |
| WO 92/01007 | 1/1992 | WIPO . |
| WO 92/05178 | 4/1992 | WIPO . |
| WO 92/06097 | 4/1992 | WIPO . |
| WO 92/09610 | 6/1992 | WIPO . |
| WO 92/15099 | 9/1992 | WIPO . |

OTHER PUBLICATIONS

Heterocyclic Compounds, vol. IV, Part A, Edited by Rodd, 1957, Elsevier Publishing Co. N.Y.

Treibs et al. Liebigs Annalen Chemie, 721, pp. 116–120, 1969.

Anderson, H.L. "Meso–Alkynyl porphyrins", *Tet. Letts*, 1992, 33, 1101–1104.

Arnold et al, "Some Reactions of Meso–Formyloctaethylporphyrin" *JCS Perkin I*, 1978, 366–370.

Arnold and Nitschinsk, "The Preparation of Novel Porphyrins and Bis(Porphyrins) Using Palladium Catalysed Coupling Reactions", *Tet. Letts.*, 1993, 34, 693–696.

Azizian et al., "Synthesis of Organotrialkystannanes. The Reaction Between Organic Halides and Hexaalskydistannanes in the Presence of Paladium Complexes", *Organomet. Chem.*, 1981, 215, 49–58.

Barbero et al., "The Stannyl–Cupration of Acetylenes and the Reaction of the Intermediate Cuprates with Electrophiles as a synthesis of Substituted Vinylstannanes", *J. Chem. Soc. Chem. Commun.*, 1992, 351–353.

(List continued on next page.)

*Primary Examiner*—Mukund J. Shah
*Assistant Examiner*—Pavanaram K Sripada
*Attorney, Agent, or Firm*—Woodcock Washburn Kurtz Mackiewicz & Norris LLP

[57] ABSTRACT

Electron-deficient porphyrins are provided, as well as processes and intermediates for their preparation. In preferred embodiments, the electron-deficient porphyrins are prepared by condensing pyrrole derivatives and removing water thus formed from the resulting reaction mixture.

21 Claims, No Drawings

OTHER PUBLICATIONS

Bonnett, R. Chapter 1 entitled "Nomenclature" The Porphyrins, Dolphin, ed., vol. I, Academic Press, New York 1–27 1978.

Cadiot and Chodkiewicz in Viche (ed.), Chapter 9 entitled "Coupling of Acetylene from Acetylenes" 597–647, Marcel Dehker, NY 1964.

Callot, "Bromination of m–tetraphenylporphine. Preparation of alkyl derivatives and polycyanoporphines" *Chem. Abstracts,* vol. 81, #105479p (p.530) 1974.

Clezy, P. S. et al., Chapter 6 "Synthesis of Porphyrins from Oxobilane Intermediates" The Porphyrins, Dolphin, ed. vol. I, Academic Press, New York, 265–288 1978.

Cohen, Jack S., "Use of Paramagnetic Metalloporphyrins as Contrast Agents for Tumors in NMR Imaging" (Feb. 1985), U.S. Dept. of Commerce, Springfield, VA 22161**.

Collman et al., "Principles & Applications of Organotransition Metal Chemistry", Chapter 14 710–738 University Science Books, 1987, Mill Valley, CA.

Drummond et al., "Tin(Sn++++)–Diiododeuteroporphyrin; an in Vitro and in vivo Inhibitor of Heme Oxygenase with Substantially Reduced Photoactive Properties", *J. of Pharmacology and Experimental Therapeutics,* 1991, 257, 1109–1113.

DiNello, Robert K. et al., Chapter 7 entitled "Isolation and Modification of Natural Porphyrins," The Porphyrins, Dolphin, ed. vol. I, 1978, Academic Press, New York, 289–339.

Durand et al., "Mechanistic Aspects of the Catalytic Reduction of Dioxygen by Cofacial Metalloporphyrins" *J. Am. Chem. Soc.,* 1983, 105, 2710–2718.

Ebert & Rieke, "Direct Formation of Organocopper Compounds by Oxidative Addition of Zerovalent Copper to Organic Halides" *J. Org. Chem.,* 1984, 49, 5280–5282.

Ebert & Rieke, "Preparation of Aryl, Alkynyl, and Vinyl Organocopper Compounds by the Oxidative Addition of Zerovalent Copper to Carbon–Halogen Bonds" *J. Org. Chem.,* 1988, 53, 4482–4488.

Eglinton and McCrae, "The Coupling of Acetylenic Compounds" from Advances in Organic Chemistry vol. 4: 225–328 Raphael et al. Eds, Interscience Publishers, New York–London 1963.

Giroud–Godquin, Anne Marie et al., "Metallomesogens: Metal Complexes in Organized Fluid Phases" *Angew. Chem. Int. Ed. Engl.,* 1991, 30, 375–402.

Gonsalves, Rocha, d'A. A.M. et al., "A New Look into the Rothemund meso–Tetraalkyl and Tetraarylporphyrin Synthesis" *J. Heterocyclic Chem.,* 1985, 22, 931–933.

Greenwood and Earnshaw, Chemistry of the Elements, Pergamon Press, Oxford, 1984, 1399–1403.

Groves et al., "Catalytic Asymmetric Epoxidations with Chiral Iron Porphyrins" *J. Am. Chem. Soc.,* 1983, 105, 5791–5796.

Gunter and Robinson, "Purpurins Bearing Functionality at the 6,16–meso–Positions: Synthesis from 5,15–Disubstituted meso–[β–(Methoxycarbonyl)vinyl]porphyrins" *Aust. J. Chem.,* 1990, 43, 1839–1860.

Hevesi et al., "Synthesis of meso–Tetravinyl Porphyrins Through 1–Selenoallyl Cationic Species" *J. Chem. Soc. Chem. Commun.,* 1986, 1725–1727.

Hayashi, T. et al., "Dichloro[1,1']–Bis (Diphenylphosphino) Ferrocene Palladium(II): An Effective Catalyst for Cross––Coupling Reaction of a Secondary Alkyl Grignard Reagent with Organic Halides" *Tet. Letts.,* 1979, 21, 1871–1874.

Helms, Anna et al., "Electron Transfer in Bis–Porphyrin Donor–Acceptor Compounds with Polyphenylene Spacers Shows a Weak Distance Dependence" *J. Am. Chem. Soc.,* 1992, 114, 6227–6238.

Johnson, A.W. Chapter 5 "Synthesis of Porphyrins from 1,19–Dideoxybiladienes–ac and 1,19–Dideoxybilenes–b" The Porphyrins, Dolphin, ed. vol. I, Academic Press, New York, 1978, 235–264.

Kim et al., Chapter 3 entitled "Synthesis of Porphyrins from Monopyrroles" The Porphyrins, Dolphin, ed. vol. I, Academic Press, New York, 1978, 85–99.

Komarov et al., "Synthesis and Some Transformations of α–Siliconacetylenic Aldehydes" UDS 1966, 920–922.

Kumada, "Nickel and Palladium Complex Catalyzed Cross––Coupling Reactions of Organometallic Reagents with Organic Halides" *M. Pure & Appl. Chem.,* 52, 1980, 669–679.

Lehn, Jean–Marie, "Supramolecular Chemistry–Scope and Perspectives Molecules, Supermolecules, and Molecular Devices (Nobel Lecture)", *Angewandte Chemie Int. Ed. In Eng.,* 1988, 27(1), 89–112.

Lindsey and Wagner, "Investigation of the Synthesis of Ortho–Substituted Tetraphenylporphyrins", *J. Org. Chem.,* 54, 1989, 827–836.

Lindsey et al., "Rothemund and Adler–Longo Reactions Revisited: Synthesis of Tetraphenylporphyrins Under Equilibrium Conditions", *J. Org. Chem.,* 1987, 52, 827–836.

Manka, John S. and Lawrence, David S., "Self–Assembly of a Hydrophobic Groove", *Tet. Letts.,* 1989, 30, 7341–7344.

Mansuy et al., "Asymmetric Epoxidation of Alkenes Catalyzed by a Basket–Handle Iron–Porphyrin Bearing Amino Acids", J. Chem. Soc. Chem. Commun., 1985, 155–156.

Maruyama and Kawabata, "Synthesis and Characterization of Polyyne Porphyrins", *Bull Chem. Soc., Jpn.* 1990, 63, 170–175.

Mauzerall D., Chapter 3 entitled "The Porphyrinogens" The Porphyrins, Dolphin, ed. vol. III, Academic Press, New York, 1978, 91–101.

Minnetian, Ohannes M., et al., "New Synthesis and Reactions of Some Halogenated Porphyrins" *J. Org. Chem.,* 1989, 54, 5567–5574.

Morris, Ian K. et al., "Syntheses of Novel Substituted Porphyrins by the Mercuration and Palladium/Olefin Methodology" *J. Org. Chem.,* 1990, 55, 1231–1236.

Nagata, Toshi et al., "Synthesis and Optical Properties of Conformationally Constrained Trimeric and Pentameric Porphyrins Arrays" *J. Am. Chem. Soc.,* 1990, 112, 3054–3059.

Nudy, Louis R. et al., "A Study of Bromoprophins" *Tetrahedron,* 1984, 40, 2359–2363.

Osuka et al., "A 1,2–Phenylene–Bridged Porphyrin Dimer—Synthesis, Properties, and Molecular Structure" *Angew. Chem. Int. Ed. Engl.,* 1991, 30, 582–584.

Paine, Chapter 4 entitled "Synthesis of Pyrroles and of Porphyrins via Single–Step Coupling of Dipyrrolic Intermediates" The Porphyrins, Dolphin, ed. vol. I, Academic Press, New York, 1978, 101–235.

Pandey, Ravindra K. et al., "Efficient Synthesis of Porphyrin Dimers with Carbon–Carbon Linkages" *Tet. Letts.,* 1990, 31, 789–792.

Pandey, Ravindra K. et al., "A Novel Approach to the Synthesis of Symmetrical and Unsymmetrical Prophyrin Dimers", *Tet. Letts.,* 1992, 33, 5315–5318.

Pandey, Ravindra K. et al., "Syntheses, Stability, and Tumorcidal Activity of Porphyrin Dimers and Trimers with Ether Linkages" *Tet. Letts.,* 1990, 31, 7399–7402.

Patai and Rapport, The Chemistry of Functional Groups, Supplement C, part 1: 529–534, Wiley, NY, 1983.

Patai and Rapport, Eds., Simandi (Author) Ch. 13 "Oxidation of Triple Bonded Groups from The Chemistry of Functional Groups Supplement C" 513–521 (John Wiley & Sons) 1983.

Rodriguez, J., et al., "Picosecond Studies of Quinone–Substituted Monometalated Porphyrin Dimers: Evidence for Superexchange–Mediated Electron Transfer in a Photosynthetic Model System" *J. Am. Chem. Soc.,* 1991, 113, 1652–1659.

Skotheim, Terjie A. Ed., Gibson (Author) "Substituted Polyacetylenes, in Handbook of Conducting Polymers" Marcel Dekker, NY vol. 1 Ch. 11, 1986, 405–439.

Stein, C.A. and Cohen, "Oligodeoxynucleotides as Inhibitors of Gene Expression: A Review" *Cancer Res.,* 1988, 48, 2659–2668.

Vicente and Smith, "Vilsmeier Reactions of Porphyrins and Chlorins with 3–(Dimethylamino) acrolein To Give meso–(2–Formylvinyl)porphyrins: New Syntheses of Benzochlorins, Benzoisobacteriochlorins, and Benzobacteriochlorins and Reductive coupling of Porphyrins and Chlorins Using Low–Valent Titanium Complexes" *J. Org. Chem.,* 1991, 56, 4407–4418.

Wallace and Smith, "Stepwise Syntheses of Unsymmetrical Tetra–Arylporphyrins. Adaptation of the MacDonald Dipyrrole Self–Condensation Methodology" *Tet. Letts.,* 1990, 31, 7265–7268.

Wasielewski, "Photoinduced Electron Transfer in Supramolecular Systems for Artificial Photosynthesis" *Chem. Rev.,* 1992, 92, 435–461.

Wytko, Jennifer A. et al., "A Highly Rigid Capped Porphyrin", *J. Org. Chem.,* 1992, 57, 1015–1018.

Yang et al., "Infrared Spectra of Tetrakis(o–chlorophenyl)porphine and its metal complexes" *Chemical Abstracts* vol. 105: #180709f 1986, p. 544.

Kitazume, T. and Ishikawa, N. "Ultrasound–Promoted Selective Perfluoroalkylation on the Desired Position of Organic Molecules" *J. Am. Chem. Soc.,* 1985, 107, 5186–5189.

Klabunde, K.J. et al. "Synthesis Employing Oxidative Insertion of Palladium Atoms into Aryl, Alkyl, and Acyl Carbon––Halogen Bonds. Properties of and Phosphine Trapping of the Nonligand Stabilized RPdX and RCOPdX Intermediates[1,2]" *J. Am. Chem. Soc.* 1974, 96, 7674–7680.

Lindsey et al., "Investigation of a Synthesis of meso–Porphyrins Employing High Concentration Conditions and an Electron Transport Chain for Aerobic Oxidation" *J. Org. Chem.,* 1994, 59, 579–587.

Katritzky et al., "A $^{13}$C Study of Hydroxymethyl Derivatives of Five–Membered Ring Heterocycles" *Magnetic Resonance in Chem.,* 1988, 26, 129–133.

Katritzky et al., "Utility of $^{13}$C NMR Spectroscopy in Monitoring the Course of a Complex Reaction Sequence: Reaction of Pyrrole with Formaldehyde" *Magnetic Resonance in Chem.,* 1988, 26, 124–128.

Ogoshi et al., "Synthesis of β–Trifluoromethylpyrroles" *Tet. Letts.,* 1983, 24, 929–930.

Gassman, et al., "Electronic Effects of Peripheral Substituents in Porphyrins: X–ray Photoelectron Spectroscopy and ab Initio Self–Consistent Field Calculations" *J. Am. Chem. Soc.,* 1992, 114, 9990–10000.

Onda, Hiroyuki et al., "Fluoropyrroles and Tetrafluoroporphyrins", *Tet. Lets.,* 1985, 26, 4221–4224.

Homma, Michihide et al., "Electron Deficient Porphyrins. 1. Tetrakis(Trifluoromethyl)porphyrin and Its Metal Complexes", *Tet. Letts.,* 1983, 24, 4343–4346.

Yoshimura, Tetsuhiko et al., "Nitrosyl Iron(II) Complexes of Porphyrins Substituted with Highly Electron–Withdrawing $CF_3$ Groups: Electronic Absorption, MCD and EPR Spectral Study", *Inorganic Chimica Acta,* 1993, 208, 9–15.

Kaesler and LeGoff, "Synthesis of (Polyfluoroalkyl)pyrroles and Porphyrins", *J. Org. Chem.,* 1982, 47(27), 5243–5246.

Jackson, A., et al., "Pyrroles and Related Compounds. Part XXV. Pemptoporphyrin, Isopemptoporphyrin and Chlorocruorophyrin (Spirographis Porphyrin)", *J. Chem. Soc.,* issued Apr., 1974, pp. 480–490.

Sanders, et al., "Studies on the Conformation of 5,15–Diarylporphyrins with (Arylsulfonyl)oxy Substituents", *J. Org. Chem.,* 1988, 53, 5272–5281.

Aoyagi, et al., "Facile Syntheses of Perfluoroalkylporphyrins. Electron Deficient Porphyrins II", *Chem. Letters,* 1988, 1891–1894.

ELECTRON-DEFICIENT PORPHYRINS AND PROCESSES AND INTERMEDIATES FOR PREPARING SAME

RELATED APPLICATIONS

This application is a division of application Ser. No. 08/234,651, filed Apr. 28, 1994 U.S. Pat. No. 5,599,924 which is a continuation-in-part of application Ser. No. 08/064,468, filed May 20, 1993 U.S. Pat. No. 5,493,017 which is a continuation-in-part of application Ser. No. 07/929,943, filed Aug. 16, 1992 U.S. Pat. No. 5,371,199

FIELD OF THE INVENTION

This invention relates to porphyrins bearing electron-withdrawing substituents such as perhaloalkyl groups, and to techniques and intermediates useful in preparing such compounds.

BACKGROUND OF THE INVENTION

Porphyrins are derivatives of porphine, a conjugated cyclic structure of four pyrrole rings linked through their 2- and 5-positions by methine bridges. Porphyrins can be covalently attached to other molecules. The electronic features of the porphyrin ring system can be altered by the attachment of one or more substituents. The term "porphyrin" includes derivatives wherein a metal atom is inserted into the ring system, as well as molecular systems in which ligands are attached to the metal. The substituents, as well as the overall porphyrin structure, can be neutral, positively charged, or negatively charged.

Electron-deficient porphyrins (i.e., porphyrins bearing substituents that are electron-withdrawing relative to hydrogen) have been suggested for use as industrial oxidation catalysts. A number such compounds have been prepared, typically through condensation of suitably substituted aldehydes and/or pyrroles. However, known synthetic methods generally proceed in low yield, if at all, and cannot be used to produce many types of electron-deficient porphyrins. Accordingly, there exists a need in the art for efficient synthetic methods capable of producing a greater variety of such compounds.

OBJECTS OF THE INVENTION

It is one object of the present invention to provide improved methods for synthesizing electron-deficient porphyrins.

It is another object of the invention to provide novel electron-deficient porphyrins.

It is yet another object to provide novel compounds that include electron-deficient porphyrins.

It is yet another object to provide synthetic precursors of electron-deficient porphyrins.

It is a further object of the invention to provide polymers containing linked electron-deficient porphyrins.

It is still another object to provide new applications for electron-deficient porphyrins and compounds that contain them.

SUMMARY OF THE INVENTION

These and other objects are satisfied by the present invention, which provides novel electron-deficient porphyrins and methods for their preparation. In preferred embodiments, the electron-deficient porphyrins have formula (1), (2), or (3):

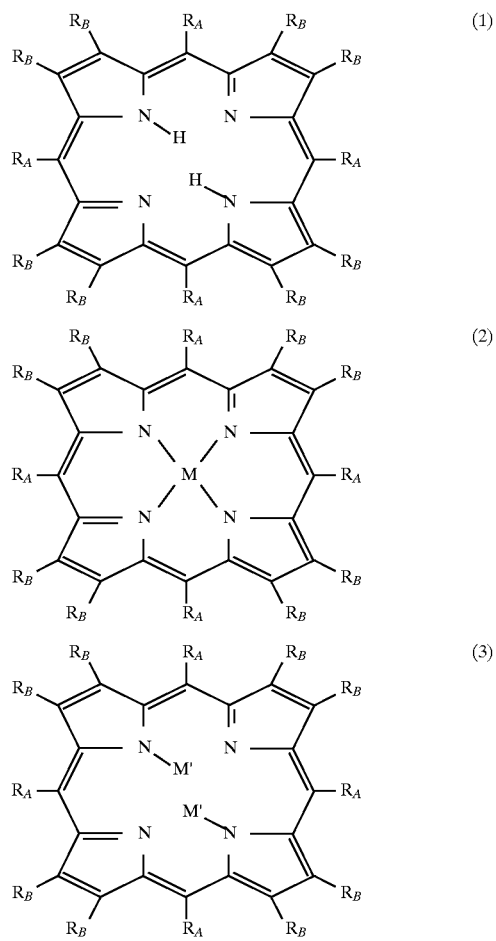

wherein M and M' are metal atoms and at least one of $R_A$ is a group that is electron-withdrawing relative to hydrogen. In preferred embodiments, at least one $R_A$ is a perhaloalkyl group or a perhaloaryl groups and at least one $R_B$ group is H, perhaloalkyl, perhaloaryl, $NO_2$, F, Cl, Br, or CN.

In accordance with the invention, these and other electron-deficient porphyrins are prepared by first preparing an electron-deficient porphyrinogen, a partially-oxidized, electron-deficient porphyrinogen, an electron-deficient polypyrryl intermediate, or a partially-oxidized, electron-deficient polypyrryl intermediate (together, porphyrinogens and polypyrryl intermediates) through pyrrole-based condensation reactions wherein at least a portion of the generated water in such reactions is removed from the reaction mixture. In certain embodiments, porphyrinogens and polypyrryl intermediates are prepared by condensing an aldehyde having formula $R_A$—CHO with a pyrrole derivative having formula (4) (q=0, 1, or 2). Alternatively, such compounds are prepared by condensing hydroxymethylpyrrole having formula (5) (n=0, 1, or 2).

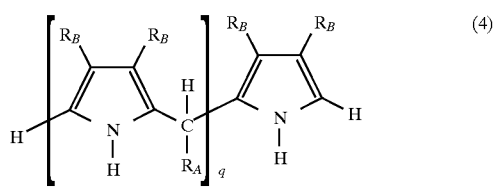

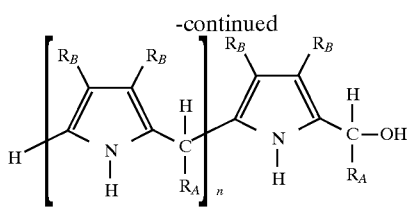

(5)

Porphyrinogens and polypyrryl intermediates also can be prepared by condensing bis-hydroxymethylpyrrole having formula (6) (n=0, 1, or 2) with a pyrrole having formula (7).

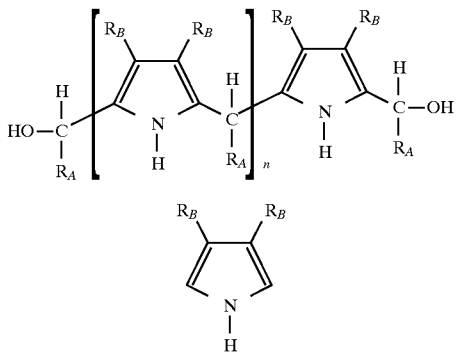

(6)

(7)

Porphyrinogens and polypyrryl intermediates thus formed can be directly oxidized or can be isolated and then oxidized. Oxidation of porphyrinogens yields porphyrins and/or partially oxidized porphyrinogens. Oxidation of polypyrryl intermediates yields partially-oxidized polypyrryl intermediates that can be further condensed and/or oxidized to form porphyrins, porphyrinogens, and/or further polypyrryl intermediates.

In another aspect, the invention provides polymers comprising linked porphyrin units, at least one of such units being an electron-deficient porphyrin. In certain embodiments, porphyrin units having formula (1), (2), or (3) share covalent bonds. In other embodiments, at least one $R_A$ group or R group functions as a linking group. In these embodiments, at least a portion of a linking group can have formula $[C(R_C)=C(R_D)(R_E)]_x$, $[\equiv C(R_D)]_x$, $[CH_2(R_C)—CH(R_D)(R_E)]_x$ or $[CH=CH(R_D)]_x$ where $R_C$, $R_D$, and $R_E$ are, independently, H, F, Cl, Br, I, alkyl or heteroalkyl having from 1 to about 20 carbon atoms, aryl or heteroaryl having about 4 to about 20 carbon atoms, alkenyl or heteroalkenyl having from 1 to about 20 carbon atoms, alkynyl or heteroalkynyl having from 1 to about 20 carbon atoms, trialkylsilyl or porphyrinato, provided that at least one of $R_C$, $R_D$, and $R_E$ is not H and x is at least 1. $R_C$, $R_D$, and $R_E$ also can include peptides, nucleosides, and/or saccharides. The remaining of $R_A$ and $R_B$ can be H, halogen, alkyl or heteroalkyl having 1 to about 20 carbon atoms or aryl or heteroaryl having 4 to about 20 carbon atoms, $C(RC)=C(R_D)(R_E)$, $C\equiv C(R_D)$, or a chemical functional group that includes a peptide, nucleoside, and/or saccharide. In other preferred embodiments, the linking group is cycloalkyl or aryl having about 6 to about 22 carbon atoms.

The invention also provides processes for preparing porphyrin-containing polymers. In certain embodiments, the processes comprise providing at least two compounds that, independently, have formula (1), (2), or (3) wherein at least one $R_A$ group or $R_B$ group in each of the compounds contains an olefinic carbon-carbon double bond or a chemical functional group reactive therewith. In other embodiments, at least one $R_A$ group or $R_B$ group in each of the compounds contains a carbon-carbon triple bond or a chemical functional group reactive therewith. The compounds are then contacted for a time and under reaction conditions effective to form covalent bonds through the carbon-carbon double and/or triple bonds.

The porphyrins and porphyrin-containing polymers of the invention can be used, for example, as dyes, catalysts, contrast agents, antitumor agents, antiviral agents, and in chemical sensors and electrooptical devices.

DETAILED DESCRIPTION OF THE INVENTION

It has been found in accordance with the present invention that a wide variety of novel porphyrins can be prepared by condensation of suitably functionalized pyrroles provided that at least a portion of the water of condensation is removed from the reaction mixture. In general, the resulting porphyrins have formula (1), (2), or (3):

(1)

(2)

(3)

wherein M and M' are metal atoms, at least one $R_A$ is a group that is electron-withdrawing relative to hydrogen, and at least one $R_B$ is H or an acid-stable chemical functional group.

M preferably is a lanthanide or actinide or a metal such as Sc, Ti, V, Cr, Mn, Fe, Co, Ni, Cu, Y, Zr, Nb, Mo, Ru, Rh, Pd, Ag, La, Hf, Ta, W, Re, Os, Ir, Pt, Cd, Hg, Li or Au. More preferably, M is Cr, Mn, Fe, Co, Ni, Ru, Rh, Pd, Os, Ir, Pt, or Au. M' can be a metal such as Li, Na, K, Rb, or Cs, preferably Li.

At least one $R_A$ in the compounds of the invention is an alkyl group that is electron-withdrawing relative to hydrogen. The remaining $R_A$ and $R_B$ groups can be the same or different and are selected from H and those groups known to be stable under the acidic reaction conditions of the invention, including alkyl, alkenyl, alkynyl, and aryl groups. (see, e.g., application Ser. No. 08/064,468) In preferred embodiments, the $R_A$ groups are selected such that they are not each perhaloalkyl having 1 to 4 carbon atoms, phenyl, dihalophenyl, perhalophenyl, or CN, and the $R_B$ groups are selected such that they are not perfluoromethyl, $NO_2$, CN, or halogen. Those skilled in the art will recognize that chemical protecting groups can be attached to acid-sensitive functionality found within $R_A$ and/or $R_B$ and can be removed after condensation has been completed. (see, e.g., Greene and Wuts in *Protective Groups in Organic Synthesis*, John Wiley & Sons, Inc., 1991).

Compounds having formulas (1)–(3) preferably bear 1, 2, 4, 8, or 12 substituents (i.e., 1, 2, 4, 8, or 12 of $R_A$ and $R_B$ are not H) . In certain embodiments, four $R_A$ groups bear electron-withdrawing functionality.

Numerous examples of electron-withdrawing functional groups are known to those skilled in the art. Further, electron-withdrawing groups can be identified through routine experimentation involving, for example, replacement of hydrogen in a molecule with a given group and then testing any resultant inductive effects. Representative electron withdrawing groups include the following: $N\text{-}(alkyl)_3^+$, $NH_3^+$, $NO_2$, $SO_2\text{-}(alkyl)$, CN, $SO_2\text{-}(aryl)$, C(O)OH, F, Cl, Br, I, C(O)O-(alkyl), C(O)-(alkyl), and/or CHO, wherein alkyl groups have from about 1–30 carbon atoms and aryl groups have about 3–50 carbon atoms. In preferred embodiments, alkyl and aryl groups have from 1 to about 20 carbon atoms and about 6 to about 20 carbon atoms, respectively. More preferably, alkyl groups have from 5 to about 20 carbon atoms and aryl groups have from about 6 to about 20 carbon atoms. The terms alkyl and aryl are intended to include moieties substituted with, for example, halogens or nitro groups, as well as moieties wherein heteroatoms (e.g., N, O, S, Se, and Te) are inserted into the carbon backbone of an alkyl or aryl structure to yield, for example, an ether, thioether, and pyridinyl group. Alkyl and aryl groups can bear substituents that include additional carbon atoms. Preferred electron-withdrawing groups are substituted and unsubstituted alkyl and aryl groups that possess net electron-withdrawing effects. Perhaloalkyl and perhaloaryl groups are particularly preferred, including perfluoroalkyl, perfluorophenyl, perfluorobenzyl, and tetrafluoropyridyl groups.

In certain embodiments, porphyrins according to the invention are prepared by synthesizing and then oxidizing suitably-substituted porphyrinogen compounds having, for example, formulas (8) and (9).

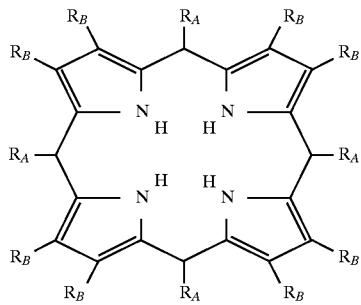

(8)

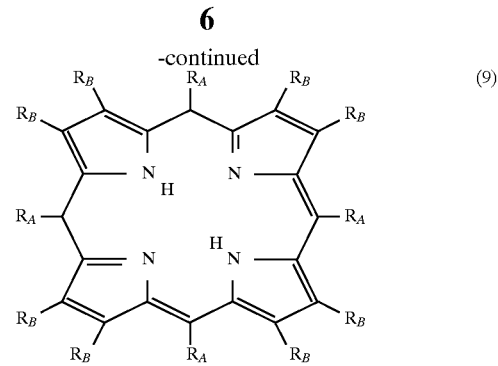

(9)

In other embodiments porphyrins are prepared by condensation and oxidation of suitably-substituted polypyrryl intermediates having, for example, formulas (10) and (11).

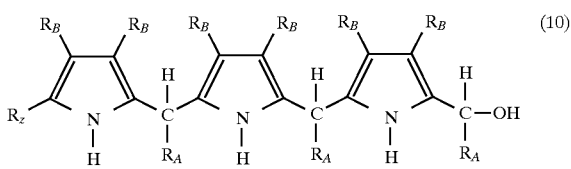

(10)

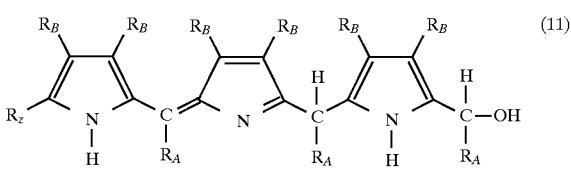

(11)

Porphyrinogens and polypyrryl intermediates can be prepared by condensing aldehydes having formula $R_A$-CHO with pyrroles derivative having formula (4) (q=0, 1, or 2). Alternatively, such compounds are prepared by condensing alcohols having formula (5) (n=0, 1, or 2).

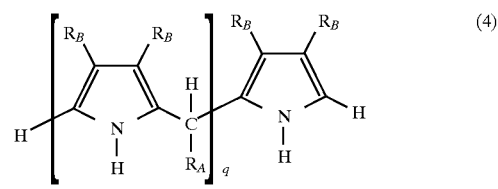

(4)

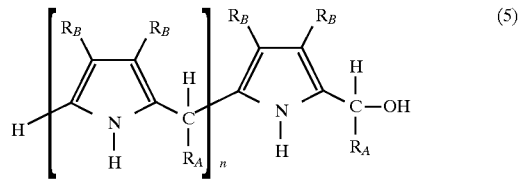

(5)

Porphyrinogens and polypyrryl intermediates also can be prepared by condensing alcohols having formula (6) (n=0, 1, or 2) with pyrroles having formula (7).

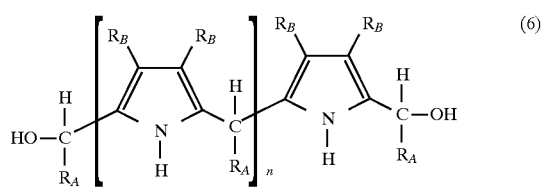

(6)

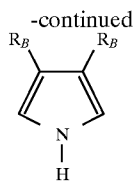

(7)

Each of these reactions should be performed in organic solvent in the presence of acid for a time and under conditions effective to form a reaction mixture comprising water and an adduct of the reagents. In accordance with the invention, at least a portion of the water thus formed is removed from the reaction mixture.

A wide variety of organic solvents can be used in the synthetic processes of the invention, including benzene, toluene, xylenes, methylene chloride, chloroform, trichloroethylene, and mixtures thereof. Aprotic solvents are preferred, particularly nonpolar, aprotic solvents. Solvents capable of forming azeotropes (i.e., constant boiling mixtures) with water are particularly preferred.

Acids according to the invention are ions or molecules having the capacity to accept at least one electron pair. Representative acids include benzoic acid, sulfonic acids (e.g., p-toluenesulfonic acid and methanesulfonic acid), trifluoracetic acid, boron trifluoride, boron trichloride, and mixtures thereof. Preferred acids are not volatile under reactions conditions of the invention. Protic acids, particularly strong protic acids (i.e., those having $pK_a<0$), are preferred. In preferred embodiments, a catalytic (i.e., non-stoichiometric) amount of acid is used.

Water can be removed from adduct-containing reaction mixtures by a wide variety of known techniques, including membrane-based separations. Water also can be removed by contacting a reaction mixture with moieties that absorb, trap, or react with water or otherwise render water non-reactive. In general, the chosen technique should remove at least a portion of any water present but should not remove the adduct-forming reagents. Representative water removal techniques are disclosed by U.S. Pat. No. 4,332,643 (Reid, European Patent Application EP 92-114390 (Inaba, et al.), Japanese Patent Applications 91-146674 (Miyazaki, et al.), 91-20083 (Kondo, et al.), and 90-104128 (Okazaki, et al.), and Brazilian Patent Application 77-433 (Scaglia, et al.). Water preferably is removed by distilling an azeotrope formed by the water and the organic solvent. In certain embodiments, the distilled azeotrope is collected in a vessel and allowed to separate into aqueous and organic phases, and the organic (solvent) phase is returned to the reaction mixture. In other embodiments, the distilled azeotrope is contacted with a drying agent and the dried distillate is returned to the reaction mixture. Representative drying agents include phosphorous pentoxide, calcium hydride, calcium oxide, barium oxide, lithium aluminum hydride, molecular sieves, and mixtures thereof. Numerous additional drying agents are well-known to persons of ordinary skill in the art. In further embodiments, the dried distillate is collected and a roughly equal volume of fresh solvent is added to the reaction mixture. In still further embodiments, semi-permeable membrane technology is used to remove water from the reaction mixture as it is formed.

Hydroxymethylpyrroles having formulas (5) and (6) preferably prepared by contacting a pyrrole having formula (7) with base in organic solvent in the presence of an aldehyde having formula $R_A$-CHO. Representative bases include sodium hydroxide, lithium hydroxide, potassium hydroxide, barium hydroxide, alkyl or aryl lithium reagents, and alkyl or aryl Grignard reagents, with sodium hydroxide being preferred. The pyrrole, aldehyde, and base can be reacted simultaneously or in a number of different ways. For example, the pyrrole can be contacted with base and then added to the aldehyde, or can be contacted with base in the presence of aldehyde. In certain embodiments, pyrrole, aldehyde, and base are contacted in the absence of solvent.

Oxidation of porphyrinogens and polypyrryl intermediates can be accomplished by a number of techniques. For example, porphyrinogen- and/or polypyrryl-containing reaction mixtures can be exposed to oxidizing conditions. Alternatively, such compounds are isolated from a reaction mixture and then contacted with an oxidizing agent. Representative oxidizing agents include oxygen, p-chloranil, 2,3-dichloro-5,6-dicyanobenzoquinone (DDQ), and mixtures. Oxidation of electron-deficient compounds also can be effected using bulk electrochemical methods (see, e.g., Laboroatory Techniques in Electroanalytical Chemistry, P. T. Kissinger and W. R. Heineman, eds., New York, Marcel Dekker, 1984). In general, oxidation conditions for partially-oxidized porphyrinogens and polypyrryl intermediates (e.g., formulas (9) and (11)) will be less vigorous than for porphyrinogens and polypyrryl intermediates in more reduced form (e.g., formulas (8) and (10)). More electron-deficient porphyrinogens generally require more vigorous oxidation conditions.

The processes of the invention produce somewhat monomeric compounds that can be incorporated into porphyrin-containing homopolymers or copolymers or into macromolecular or supramolecular species containing, for example, one or more peptides, nucleosides, or saccharides. Polymers according to the invention can contain as few as 2 porphyrin units, but more preferably contain at least 3 porphyrin units, more preferably at least 5 porphyrin units. In certain embodiments, polymers of the invention comprise a plurality of porphyrin units that, independently, have formula (1), (2), or (3) wherein at least one $R_A$ group or $R_B$ group includes a linking group selected from $[C(R_C)=C(R_D)(R_E)]_x$, $[C\equiv C(R_D)]_x$, $[CH_2(R_C)-CH(R_D)(R_E)]_x$ or $[CH=CH(R_D)]_x$ where x is at least 1. The remaining $R_A$ and $R_B$ include at least one group that is electron-withdrawing relative to hydrogen.

In other embodiments, polymers according to the invention comprise a plurality of porphyrin units that, independently, have formula (1), (2), or (3) wherein at least one $R_A$ group or $R_B$ group is a cycloalkyl, cycloalkenyl, aryl or hetercaryl linking group having about 6 to about 22 carbon atoms.

Those skilled in the art will recognize the wide variety of polymers that can be prepared from the porphyrin-containing compounds of the invention. In certain embodiments, cofacial polymers are formed having, for example, formula (12). (see, e.g., Durand, et al., *J. Am. Chem. Soc.*, 1983, 105, 2710).

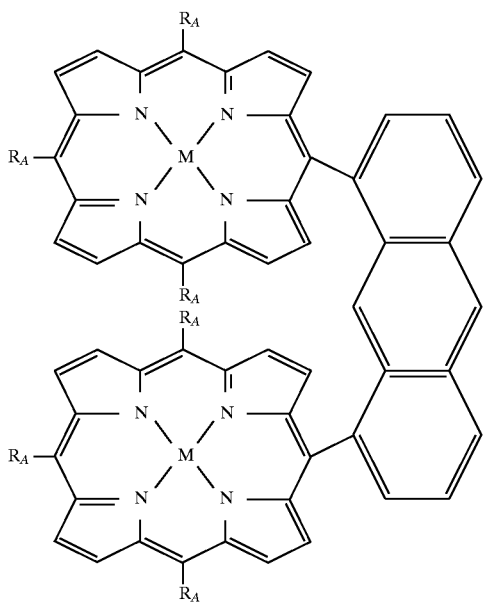
(12)

In other embodiments, somewhat linear polymer chains are forced wherein a portion of the polymer has general formula $(P_N)_r$ where $P_N$ is a porphyrin unit and r is at least 2. In further embodiments, linear polymer chains have general formula:

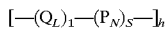

where $Q_L$ is a linking group, $P_N$ is a porphyrin unit, and h, 1, and s are independently selected to be at least 1. For example, a portion of such polymers can have formula:

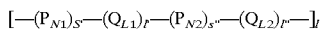

wherein $P_{N1}$ and $P_{N2}$ are independently selected porphyrin units, $Q_{L1}$ and $Q_{L2}$ are independently selected linking groups, and l', l", s', and s" are at least 1. These essentially linear polymer chains can be cross-linked such that a portion of the polymer has general formula:

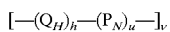

wherein $Q_H$ is a linking group, and h, u, and v are independently selected to be at least 1. A portion of these cross-linked polymers can have formula:

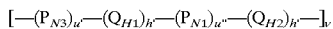

wherein $P_{N3}$ is a porphyrin unit, $Q_{H1}$ and $Q_{H2}$ are independently selected linking groups, and h', h", u', and u" are at least 1. Thus, cross-linked polymers can have formulas:

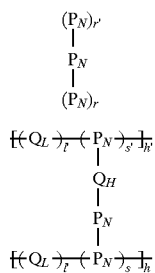

where r' is at least 1.

The polymers of the invention can be formed by contacting a substituted porphyrin with a second compound containing functionality that is reactive with the functionality contained within the porphyrin. Preferably, the porphyrin contains an olefinic carbon-carbon double bond, a carbon-carbon triple bond or some other reactive functionality. The contacting should be performed under conditions effective to form a covalent bond between the respective reactive functionalities. Preferably, porphyrin-containing polymers are formed by meal-mediated cross-coupling of, for example, dibrominated porphyrin units. Also, porphyrin-containing polymers can be synthesized using known terminal alkyne coupling chemistry. (see, e.g., Patai, et al., The Chemistry of Functional Groups, Supplement C, Part 1, pp. 529–534, Wiley, 1983; Cadiot, et al., Acetylenes, pp. 597–647, Marcel Dekker, 1964; and Eglinton, et al., Adv. Org. Chem., 1963, 4, 225) As will be recognized, the second compound noted above can be a substituted porphyrin of the invention or some other moiety such as an acrylate monomer. Thus, a wide variety of copolymeric structures can be synthesized with the porphyrins of the invention. Through careful substituent selection the porphyrins of the invention can be incorporated into virtually any polymeric matrix known in the art, including but not limited to polyacetylenes, polyacrylates, polyolefins, polyethers, polyurethanes, polycarbonates, polyanilines, polypyrroles, and polythiophenes. For example, fluorescent porphyrins can be incorporated into such polymers as end-capping groups.

The porphyrins and porphyrin-containing polymers of the invention can be used, for example, as dyes, catalysts, contrast agents, antitumor agents, antiviral agents, liquid crystals, in chemical sensors and in electrooptical and solar energy conversion devices. One preferred use for compounds containing electron-deficient porphyrins are as catalysts for the oxygenation of alkanes and/or alkenes, particularly oxygenations performed in supercritical carbon dioxide. Electron-deficient porphyrins also can be incorporated into supramolecular structures. The polymers and supramolecular structures, which anchor porphyrin units in a relatively stable geometry, should improve many of the known uses for porphyrins and even provide a number of new uses, such as in a solid phase system for sterilizing virus-containing solutions. Representative uses are disclosed by, for example, the following patents, which are incorporated herein by reference: U.S. Pat. No. 4,895,682 (Ellis, et al.); U.S. Pat. No. 4,986,256 (Cohen); U.S. Pat. No. 4,668,670 (Rideout, et al.) ; U.S. Pat. No. 3,897,255 (Erickson) ; U.S. Pat. No. 3,899,334 (Erickson); U.S. Patent No. 3,687,863 (Wacher); U.S. Pat. No. 4,647,478 (Formanek, et al.); and U.S. Pat. No. 4,957,615 (Ushizawa, et al.). Further uses are disclosed are disclosed by, for example, U.K. Patent Application 2,225,963 (Casson, et al.); International Application WO 89/11277 (Dixon, et al.); International Application WO 91/09631 (Matthews, et al.); European Patent Application 85105490.8 (Weishaupt, et al.); European Patent Application 90202953.7 (Terrell, et al.); European Patent Application 89304234.1 (Matsushima, et al.); Lehn, Angew. Chem. Int. Ed. Engl., 1988, 27, 89; Wasielewski, Chem. Rev., 1992, 92, 435; Mansury, et al., J. Chem. Soc., Chem. Comm., 1985, 155; Groves, et al., J. Am. Chem. Soc., 1983, 105, 5791) and Giroud-Godquin, et al., Angew. Chem. Int. Ed. Engl., 1991, 30, 375. at is believed that the porphyrins of the invention can be substituted for the porphyrins disclosed in each of the foregoing publications.

Additional objects, advantages, and novel features of this invention will become apparent to those skilled in the art upon examination of the following examples thereof, which are not intended to be limiting.

EXAMPLE 1

Preparation Of 2-(2,2,3,3,4,4,4-Heptafluoro-1-hydroxybutyl)pyrrole From Heptafluorobutyraldehyde Hydrate Heptafluorobutyraldehyde hydrate (9.26 g, 42.9 mmol) was placed in a 100 mL Schlenk flask. This was frozen with liquid nitrogen and an inert atmosphere was established. Against an outflow of nitrogen, dried pyrrole (5.95 mL, 85.8 mmol) and sodium hydroxide (4.52 g, 113 mmol) were added. The flask was wrapped in foil and the mixture was stirred overnight, during which time it solidified. A colorless liquid also was present. The volatile were removed by vacuum, leaving a light brown solid. The solid was dissolved in 40 mL of water and the solution was extracted (4×50 mL) with methylene chloride. The organic layers were dried over sodium sulfate and then evaporated to dryness under vacuum to give 5.39 g (47%) of a light yellow-brown solid. $^1$H NMR, (CDCl$_3$, 360 MHz) d 8.50 br $_1$H; 6.87 m 1H; 6.32m 1H; 6.22 m 1H; 5.28 d, J=8.17 Hz; 5.23 d, J=7.67 Hz; 2.42 br s.

EXAMPLE 2

Preparation Of 2-(2,2,3,3,4,4,4-Heptafluoro-1-hydroxybutyl)pyrrole From Using Organolithium Reagents Dry, distilled pyrrole (80 mmol) is dissolved in diethyl ether (200 ml) and cooled to −78° C. Butyl lithium (80 mmol, 32 ml of 2.5M solution in hexane) is added dropwise with stirring and the solution is gradually warmed to room temperature with evolution of hydrogen. This solution is transferred dropwise by cannula to a −78° C. solution of dry Heptafluorobutyraldehyde (previously distilled from P$_2$O$_5$) in tetrahydrofuran (THF) . The solution is warmed to room temperature with stirring. The volatiles are removed by vacuum leaving a solid that is dissolved in 40 mL of water and extracted (4×50 ml) with methylene chloride. The organic layers are dried over sodium sulfate and then evaporated to dryness under vacuum to give the product.

EXAMPLE 3

Preparation Of 2,5-Bis (2,2,3,3,4,4,4-heptafluoro-1-hydroxybutyl) pyrrole

Heptafluorobutyraldehyde hydrate (5.0 g, 23 mmol) was placed in a 100 mL Schlenk flask. This was frozen with liquid nitrogen and an inert atmosphere was established. Against an outflow of nitrogen, dried pyrrole (0.694 mL, 10 mmol) and sodium hydroxide (2.25 g, 56 mmol) were added. The flask was wrapped in foil and the mixture was stirred for 2 days. The volatiles were removed by vacuum, leaving a light brown, oily solid. The solid was dissolved in 40 mL of water and the solution was extracted (4×50 ml) with methylene chloride. The organic layers were dried over sodium sulfate and then evaporated to dryness under vacuum to an oily brown solid (38%), which proved to be a diastereomeric mixture of the desired products.

EXAMPLE 4

Preparation Of 2-(2,$^2$-Difluoro-2-pentafluorophenyl-1-hydroxyethyl) pyrrole

2-Pentafluorophenyl-2,2-difluoroethanal (40 mmol) and THF (5 ml) are placed in a 100 mL Schlenk flask. This is frozen with liquid nitrogen and an inert atmosphere is established. Against an outflow of nitrogen, dried pyrrole (5.95 mL, 85.8 mmol) and sodium hydroxide (4.52 g, 113 mmol) is added. The flask is wrapped in foil and the mixture is stirred overnight. The volatiles are removed by vacuum, the resulting solid is dissolved in 40 mL of water, and the solution is extracted (4×50 ml) with methylene chloride. The organic layers are dried over sodium sulfate and then evaporated to dryness under vacuum to give 2-(2,2-difluoro-2-pentafluorophenyl-1-hydroxyethyl)pyrrole.

EXAMPLE 5

Preparation Of 2-(2,2,2-Trifluoro-1-hydroxyethyl) pyrrole

The procedure of Example 4 is repeated except that trifluoroacetaldehyde is used in place of 2-Pentafluorophenyl-2,2-difluoroethanal.

EXAMPLE 6

Preparation Of 2-Pyrrolylperfluoroundecyl Methanol

The procedure of Example 4 is repeated except that perfluorododecanal is used in place of 2-Pentafluorophenyl-2,2-difluoroethanal.

EXAMPLE 7

Preparation Of Tetrakis(heptafluoropropyl)porphyrin From 2-Pyrrolyperfluoropropyl Methanol Benzene (650 ml) was placed in a one liter, double-necked flask and azeotropically dried under nitrogen using a recycling Dean-Stark apparatus. p-Toluenesulfonic acid hydrate (50 mg) was added to the benzene and azeotropic distillation was continued until the distillate stopped phase separating. The Dean-Stark trap was emptied and 4A molecular sieves (20 ml) were added to the trap. Distillation was continued for 10 minutes with the distillate recycling through the molecular sieves. 2-Pyrrolylperfluorocropylmethanol (265 mg, 1 mmol) was dissolved in 10 ml of dry benzene and added (all at once) to the benzene solution heated at reflux. The solution became pink immediately after the addition, then gradually darkened. Heating was continued for 30 minutes and the reaction mixture was quenched with 600 mg of DDQ. Heating was continued for an additional hour under N$_2$. The solution was transferred to a 1 liter round bottom flask and the solvent was removed and recovered by rotary evaporation. The remaining dark brown residue was dissolved, to the extent possible, in 50 ml of warm hexane containing 1 ml of pyridine; and was poured directly on to a short (2×10 cm) column consisting of silica that was packed in hexane and topped with a 2 cm pad of Celite. Elution of the porphyrin was carried out with hexane. Collection was continued until the eluant became nearly colorless. The solvent was removed from the collected fraction and the resulting solid was washed with cold hexane (10 ml) and filtered to yield 90 mg (37%) of nearly pure 5,10,15,20-tetrakis(perfluoropropyl)porphyrin. An analytical sample was recrystallized from chloroform (−20° C.) to yield crystals suitable for X-ray diffraction. $^1$H NMR (360 mHz, CDCl$_3$) d 9.50 (s, 8 H); −2.30 (s, 2 H) . $^{19}$F NMR (DCDl$_3$ CF$_3$COOH ext. std) d −79.7 (t, 3 F); −80.9 (broad s, 2 F); −118.8 (broad s, 2 F) . The $^{19}$F spectrum shows evidence of exchange behavior. The signal at −118.8 ppm sharpens to a broadened triplet upon warming the solution to 55° C. $^{13}$C NMR (75 MHz, CDCl$_3$) gave only two discernable signals at 144.2 and 133.8 after a 16 hour run.

EXAMPLE 8

Preparation Of Tetrakis(heptafluoropropyl)porphyrin From Pyrrole And Heptafluorobutyraldehyde In a procedure analogous to that described in Example 7, the apparatus was charged with benzene (650 ml), p-toluenesulfonic acid hydrate (50 mg) and heptafluorobutyraldehyde hydrate (0.22 g, 1 mmol). After refluxing the mixture for 1 hour, dry pyrrole (70 μl, 1 mmol) was added. The reaction was monitored by thin layer chromatography (TLC); after 1.5 hours the reaction was quenched as in Example 7. The reaction mixture was neutralized with pyridine, filtered through silica gel, pumped dry, and further purified by chromatography on silica. Several pyrrole-containing products can be isolated from this preparation. The desired product, tetrakis(heptafluoro)porphyrin, eluted as the first colored band. This method gives 4 mg (1.6%) of the target porphyrin.

EXAMPLE 9

Preparation Of Tetrachloroporphine

Porphine (Zn) (40 mg) was dissolved in 300 mL of a 1:1 mixture of THF and $CHCl_3$, and the mixture was placed in a 500 ml round bottomed flask. N-Chlorosuccinimide (NCS) was added (4.2 eq.) and the mixture was stirred overnight protected from the light. The reaction was monitored by TLC and four intermediates were observed, presumably the target compound and the mono-, di-, and trichloro intermediates. After 24 hours the reaction was stopped and tetrachloroporphine (>80%) was isolated.

EXAMPLE 10

Preparation Of Cofacial Porphyrin Dimers

To a THF solution of 5-bromo-10,15,20-trichloroporphyrinate (Zn) (1 eq.) is added $Pd^C$ bis(triphenylphosphine) (5 mol %) and anthracene-1,8-bis(chlorozinc) (0.5 eq). The reaction is stirred for 24 hours at room temperature. One band is evident by TLC of the reaction mixture. The compound is purified by silica gel chromatography to isolate the dimeric, anthracene bridged compound.

Those skilled in the art will appreciate that numerous changes and modifications may be made to the preferred embodiments of the invention and that such changes and modifications may be made without departing from the spirit of the invention. For example, it is believed that the methods of the present invention can be practiced using porphyrin-related compounds such as chlorins, phorbins, bacteriochlorins, porphyrinogens, sapphyrins, texaphrins, and pthalocyanines in place of porphyrins. It is therefore intended that the appended claims cover all such equivalent variations as fall within the true spirit and scope of the invention.

What is claimed is:

1. A compound having formula:

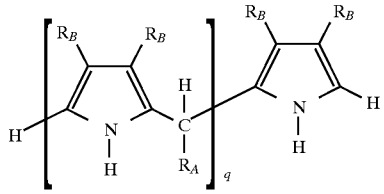

wherein:
at least one $R_A$ is a group that is electron-withdrawing relative to hydrogen;
at least one $R_B$ is H or an acid-stable functional group; and
q is 1 or 2.

2. The compound of claim 1 wherein $R_A$ is alkyl having 1 to about 30 carbon atoms or aryl having 3 to about 50 carbon atoms.

3. The compound of claim 1 wherein $R_A$ is haloalkyl having 1 to about 20 carbon atoms or haloaryl having 6 to about 20 carbon atoms.

4. The compound of claim 3 wherein $R_B$ is H, perhaloalkyl, perhaloaryl, $NO_2$, F, Cl, Br, or CN.

5. The compound of claim 1 wherein $R_A$ is perhaloalkyl having 5 to about 20 carbon atoms or perhaloaryl having 6 to about 20 carbon atoms.

6. A compound having formula:

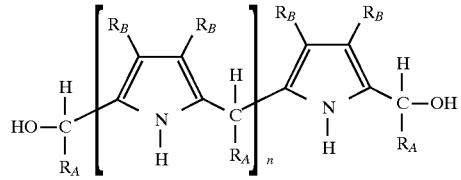

wherein
at least one $R_A$ is a group that is electron-withdrawing relative to hydrogen;
at least one $R_B$ is H or an acid-stable functional group; and
n is 0, 1, or 2.

7. A compound having formula:

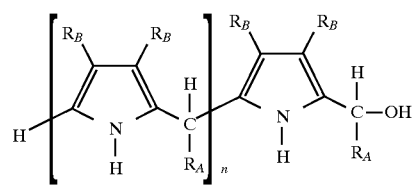

wherein:
at least one $R_A$ is a group that is electron-withdrawing relative to hydrogen;
at least one $R_B$ is H or an acid-stable functional group; and
n is 0, 1, or 2.

8. The compound of claim 1 wherein $R_A$ is alkyl having 1 to about 30 carbon atoms, aryl having 3 to about 50 carbon atoms, $N\text{-}(alkyl)_3^+$, $NH_3^+$, $NO_2$, $SO_2\text{-}(alkyl)$, CN, $SO_2\text{-}(aryl)$, C(O)OH, F, Cl, Br, I, C(O)O-(alkyl), C(O)-(alkyl), or CHO, wherein alkyl groups have from about 1–30 carbon atoms and aryl groups have about 3–50 carbon atoms.

9. The compound of claim 1 wherein $R_A$ is perfluoroalkyl having 5 to about 20 carbon atoms or perfluoroaryl having 6 to about 20 carbon atoms.

10. The compound of claim 6 wherein $R_A$ is alkyl having 1 to about 30 carbon atoms or aryl having 3 to about 50 carbon atoms.

11. The compound of claim 6 wherein $R_A$ is haloalkyl having 1 to about 20 carbon atoms or haloaryl having 6 to about 20 carbon atoms.

12. The compound of claim 11 wherein $R_B$ is H, perhaloalkyl, perhaloaryl, $NO_2$, F, Cl, Br, or CN.

13. The compound of claim 6 wherein $R_A$ is perhaloalkyl having 5 to about 20 carbon atoms or perhaloaryl having 6 to about 20 carbon atoms.

14. The compound of claim 6 wherein $R_A$ is alkyl having 1 to about 30 carbon atoms, aryl having 3 to about 50 carbon atoms, $N\text{-}(alkyl)_3^+$, $NH_3^+$, $NO_2$, $SO_2\text{-}(alkyl)$, CN, $SO_2\text{-}(aryl)$, C(O)OH, F, Cl, Br, I, C(O)O-(alkyl), C(O)-(alkyl), or CHO, wherein alkyl groups have from about 1–30 carbon atoms and aryl groups have about 3–50 carbon atoms.

15. The compound of claim 6 wherein $R_A$ is perfluoroalkyl having 5 to about 20 carbon atoms or perfluoroaryl having 6 to about 20 carbon atoms.

16. The compound of claim 7 wherein $R_A$ is alkyl having 1 to about 30 carbon atoms or aryl having 3 to about 50 carbon atoms.

17. The compound of claim 7 wherein $R_A$ is haloalkyl having 1 to about 20 carbon atoms or haloaryl having 6 to about 20 carbon atoms.

18. The compound of claim 17 wherein $R_B$ is H, perhaloalkyl, perhaloaryl, $NO_2$, F, Cl, Br, or CN.

19. The compound of claim 7 wherein $R_A$ is perhaloalkyl having 5 to about 20 carbon atoms or perhaloaryl having 6 to about 20 carbon atoms.

20. The compound of claim 7 wherein $R_A$ is alkyl having 1 to about 30 carbon atoms, aryl having 3 to about 50 carbon atoms, N-(alkyl)$_3^+$, $NH_3^+$, $NO_2$, $SO_2$-(alkyl), CN, $SO_2$-(aryl), C(O)OH, F, Cl, Br, I, C(O)O-(alkyl), C(O)-(alkyl), or CHO, wherein alkyl groups have from about 1–30 carbon atoms and aryl groups have about 3–50 carbon atoms.

21. The compound of claim 7 wherein $R_A$ is perfluoroalkyl having 5 to about 20 carbon atoms or perfluoroaryl having 6 to about 20 carbon atoms.

* * * * *